(12) United States Patent
Prandini

(10) Patent No.: US 8,715,211 B1
(45) Date of Patent: May 6, 2014

(54) VERSATILE FOOT CUSHION

(76) Inventor: Maria Christina Prandini, Fullerton, CA (US)

( * ) Notice: Subject to any disclaimer, the term of this patent is extended or adjusted under 35 U.S.C. 154(b) by 369 days.

(21) Appl. No.: 13/107,863

(22) Filed: May 13, 2011

(51) Int. Cl.
*A61F 5/00* (2006.01)

(52) U.S. Cl.
USPC .................... 602/11; 602/23; 602/30; 602/41; 128/889

(58) Field of Classification Search
USPC ............ 602/41–54, 11, 23, 30; 128/888–889; 604/174–180, 332, 338, 346, 355, 321
See application file for complete search history.

(56) References Cited

U.S. PATENT DOCUMENTS

| | | | | |
|---|---|---|---|---|
| 2,887,405 | A * | 5/1959 | Wooding | 428/460 |
| 6,765,122 | B1 * | 7/2004 | Stout | 602/41 |
| 2012/0130315 | A1 * | 5/2012 | Weadock et al. | 604/180 |
| 2013/0131621 | A1 * | 5/2013 | Van Holten et al. | 604/368 |

* cited by examiner

*Primary Examiner* — Michael A. Brown

(57) ABSTRACT

A cushioning device is capable of conforming to a variety of areas on the human foot. The device includes a thin, transparent, circular body of compliant material and a notch with angled sides and an extended base. The shape and placement of the notch allows the body to fit complex contours.

19 Claims, 3 Drawing Sheets

FIG. 1
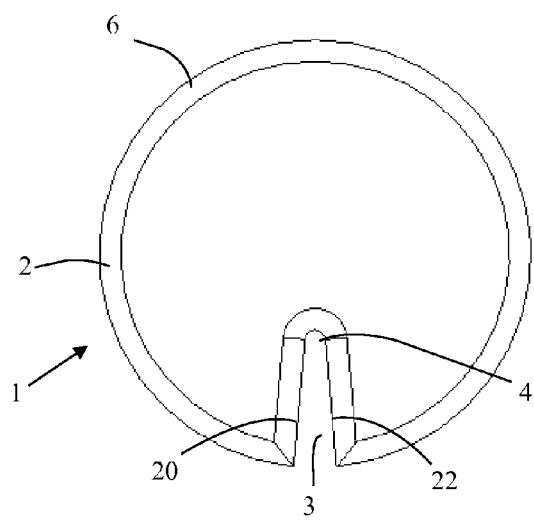
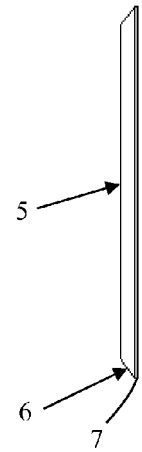
FIG. 2
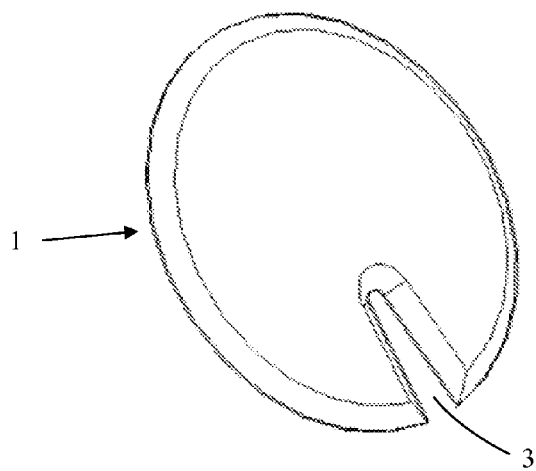
FIG. 3

VERSATILE FOOT CUSHION

BACKGROUND OF THE INVENTION

1. Field

This invention concerns the field of pads or cushions for the human foot.

2. Background

The human foot has irregular contours that vary considerably among individuals. Footwear is incredibly diverse in style and construction and is commonly selected from a limited collection of sizes for an adequate fit. Wearers frequently select footwear based on style and appearance with fit as only a secondary consideration. While some footwear features adjustability of fit through laces, adjustable straps, or the like, it is very rare that a particular shoe exactly fits a particular foot. Further, feet vary in contour and dimension during movement and throughout the course of a day in response to fatigue, applied pressure, hydration, and other factors. As a result, the fit between a shoe and the wearer's foot is frequently less than perfect.

Poor fit between a foot and footwear can lead to irritation, pain and injury. Further, even well-fitted shoes can irritate a pre-existing injury. It is thus beneficial to improve the fit between foot and footwear and to cushion and protect the foot to reduce or prevent discomfort or injury.

This is not a new problem, but earlier approaches have been less than adequate. Such approaches may be conveniently divided into devices that attach to or insert into footwear and devices that attach to the foot directly.

U.S. Pat. No. 2,090,573 is typical of devices designed to be attached to footwear. A crescent-shaped cushion is adhered by adhesive to the vamp of a shoe to cushion the foot and prevent the upper edge of the shoe at the vamp from biting into the foot. The crescent shape permits a reasonable match to the contour of the dorsum of the foot, but it is not designed for any other area. Once installed in a shoe, the cushion protects the wearer's foot only while wearing that shoe.

U.S. patent application publication 2010-0018074A1 describes a cushion insole designed to be inserted and adhered into a shoe. The insole includes marks indicating where the user may trim the insole to adjust the fit. The need to trim the device to accurately fit the wearer's foot, while allowing a more precise fit, puts a preparation burden on the wearer. Further the shape conform only to one area of the foot, limiting its application.

U.S. Pat. No. D570488 illustrates a device that attaches to the foot. A soft foam cushion surrounded by a clear flexible adhesive plastic attaches to the ball of the foot to provide comfort while walking. The roughly oval cushion is apparently only held to the foot by the surrounding adhesive, making it possible for the material of the cushion to shift or separate from the foot during motion. Further the shape appears to roughly conform only to one area of the foot, limiting its application.

U.S. Pat. No. 2,619,961 describes a bunion pad intended to be secured to the foot. A contoured cushion partially encircles a bunion, callous, or corn and separates the encircled area from the pressure of a shoe. The bunion pad may be placed in a number of different locations on the foot, but its flat shape will buckle if applied to an area that significantly departs from flat portions of the foot. The shape of the bunion pad is designed to conform to a small area of irritation that it may partially encircle. The relatively small size of corns and bunions permits the pad be similarly small in size, avoiding buckling in most applications. It is thus not applicable to use for larger areas or for areas where there is a significant departure from flatness.

U.S. Pat. No. D547948 illustrate a tri-lobe planar wound heel dressing that becomes non planar to conform to the shape of a heel. The dressing includes three triangular cut outs that divide it into three lobes. An illustration shows the opposite edges of each cut out brought into contact with one another to form the dressing into a cup-shaped structure. The patent illustrates the cup-shaped structure in contact with a heel of equal size. This design may conform to a properly-sized heel but does not appear applicable for other size heels or other areas.

U.S. Pat. No. 7,847,143 discloses a dancer's protective foot pad designed to be worn in place of other footwear. The foot pad adhesively adheres to the ball of the dancer's foot. The shape of the foot pad and a locating tab that extends between the wearer's toes limits the application of the foot pad to the ball of the foot.

U.S. patent application publication 2004/0237165A1 discloses flexible footwear that attaches adhesively to the plantar surface of the foot. Among illustrated embodiments are a first embodiment (shown in FIG. 1) resembling a footprint and a second embodiment (shown in FIG. 8) that is generally circular with a radial slit. Each includes an adhesive on the foot contact surface.

The wearer may trim the material of the first embodiment to conform to the size and shape of the wearer's foot. The adhesive presumably retains each portion in place and permits relative motion of separated portions (such as the individual toe portions). The flexibility of the device permits at least some flexing of the foot during walking. Because this device conforms in shape to the footprint, its use is as a practical matter limited to application on the bottom of the foot. Further, the need to trim the device to accurately fit the wearer's foot, while allowing a more precise fit, puts a preparation burden on the wearer.

The wearer may further adjust the second embodiment by folding the flaps on either side of the slit so that one flap overlaps the other. This forms the embodiment into a cup-shaped toe piece that better conforms to the bottom of the toes. The cup-shaped toe piece thus includes a double-layer overlap region that is of greater thickness than the non-overlapped region of the device, a situation that may produce discomfort while walking. The folding process also puts a preparation burden on the wearer.

These adhesive footwear devices are thus limited in their application area. This limitation is entirely consistent with their purpose of protecting the plantar surface of the foot in place of other footwear.

Thus there remains a need for a cushioning device that may conform to the contour of an individual foot without trimming or other adjustment, that is usable with multiple sets of footwear, that conforms to a variety of locations on the foot, and that prevents discomfort or irritation without detracting from the appearance of footwear or wearer.

SUMMARY

In some embodiments, the invention includes a generally circular compliant cushion composed of transparent viscoelastic polymeric gel that self-adheres to the foot of a wearer. The cushion may include a radial notch extending from the circumference of the cushion to a point at or near the center. The notch may be tapered and may terminate in an extended base forming a radius edge near the center of the cushion.

BRIEF DESCRIPTION OF THE DRAWINGS

FIG. 1 illustrates top view of an embodiment of the cushion of the invention.

FIG. 2 illustrates a side view of the same embodiment.

FIG. 3 illustrates a perspective view of the same embodiment.

DETAILED DESCRIPTION

Figure 4:
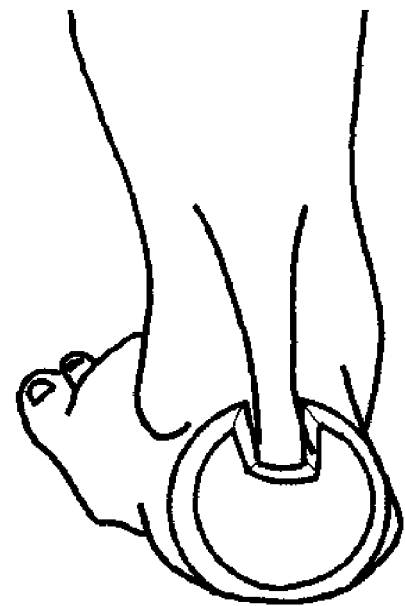
FIG. 4 illustrates an embodiment applied to a location on the heel of a human foot.

FIGS. 1, 2, and 3 illustrate one embodiment of a versatile foot cushion of the invention. The embodiment includes a flat body of substantially circular shape and cross section that is thin relative to its diameter. The body may be composed of a flexible polymer, such as a transparent viscoelastic polymer gel.

Geometry

The embodiment of cushion 1 shown in FIGS. 1, 2, and 3 includes body 2 of substantially circular shape. In some embodiments, the shape may be an ellipse or an oval, each of which shapes provides a smooth contour that fits well to the configuration of the human foot.

The diameter of body 2 may be sized to conform to the geometry of the human foot. Since feet vary in size, a variety of sizes may be used. However, I have discovered that a diameter of less than about 3.5 inches but greater than about 1.0 inch conforms to a variety of foot locations for a variety of foot sizes. In some embodiments, the diameter may be in the range of about 3.0 inches to about 1.5 inches and in some embodiments may be about 2.6 inches. Diameters greater than 1.0 inch and less about 3.5 inches may fit comfortably on many places of the foot without risk of overlapping. Diameters between about 1.5 inches and about 3.0 inches may more closely coincide with the size of sensitive areas and a diameter of about 2.6 inches combines versatility of placement with a close match to the size of most common sensitive placement areas.

Notch 3 may extend radially from the circumference to a point near the center of the substantially circular shape. In some embodiments, the notch extends along a radius about to the center of the shape and in other embodiments, it extends less than a full radius. The extent may be between about one radius and about one-half radius and in some embodiments is about two-thirds of the radius to about three quarters of the radius.

In some embodiments, notch sides 20 and 22 may be substantially parallel for a fraction of the extent of notch 3 and may angle towards one another inwardly of this fraction of the extent of notch 3. Notch sides 20 and 22 may define an included angle of about five degrees to about 20 degrees. In some embodiments the notch angle is about ten degrees. A notch angle of at least about five degrees allows cushion curvature to approximate many convex areas of the foot as explained in more detail below. A notch angle below about 20 degrees maintains a reasonable area of the cushion to perform the cushioning function. A notch angle of about ten degrees combines a fit to most convex areas and a good fit to anatomical features such as the gap between toes and the tendon of the calcaneus as explained in more detail below.

In some embodiments, notch 3 is truncated by an extended base 4 at its central end so that first notch edge 20 and second notch edge 22 do not directly join. This truncation defines the minimum width of the notch. The width of base 4 may be chosen to approximate anatomical features such as the spacing between toes or the thickness of the tendon of the calcaneus. Sizing to fit these features aids in application of the cushion to different regions of the foot as explained in more detail below.

The truncated end of notch 3 may terminate in a radius to reduce stress concentrations and thus minimize the risk of tearing.

The thickness of the cushion may increase to full thickness in as short a distance as possible from the perimeter to provide full cushioning for as large an area as practical. However, the foot is normally very sensitive to abrupt changes in height while walking as abrupt changes produce high local pressures that signal the possibility of injury. By gradually increasing the thickness of the cushion from the circumference inward, the cushion of the invention avoids such abrupt changes and provides greater comfort to the wearer.

The upper surface 5 may be formed as a chamfer 6 or radius to the edges. This has the beneficial effect of gradually increasing the thickness of the cushion so as to avoid abrupt changes.

I have discovered that a small amount of abrupt thickness change may be tolerated, but this amount is limited to about 0.040" for materials that provide suitable cushioning. In some embodiments, the amount of abrupt thickness change may be limited to no more than 0.030" and in still others to about 0.020". The perimeter of the cushion may thus begin as edge 7 at such a thickness and gradually increase in thickness to the desired thickness for full cushioning effect. This advantageously allows a larger portion of the device to provide full cushioning and avoids the manufacturing and application difficulties that a "knife-edge" taper would produce.

I have also discovered that changes in thickness using suitable materials are best tolerated when the thickness increases at rate no greater than about 0.080" for each 0.100" of distance from the perimeter of the device (an 80% slope). In some embodiments, this rate may be no greater than about 0.070" for each 0.100" (70% slope) and in other embodiments the rate may be about 0.060" for each 0.100" of distance from the perimeter (60% slope). The various rates of thickness increase depend on the compliance of the material used for the cushion. Higher rates, such as an 80% slope, may be suitable for particularly soft material. Such softer materials may require greater thicknesses for full cushioning effect. Lower rates, such as 60% slope, may be suitable for a more optimal material which provides full cushioning in thickness of about 0.100". Intermediate rates, such as a 70% slope, may be suitable for intermediate materials.

In some embodiments, the initial thickness and the thickness rate may apply both to the circumference of the cushion and to the edges of the notch.

Material

The cushion of the invention may be composed of a flexible transparent polymer. The flexibility allows the cushion to conform to the geometry of the foot.

The transparency provides some embodiments with a cushion that does not detract from the appearance of the shoe or the foot. Other embodiments may be of colored, opaque, or patterned material to provide decoration.

The polymer may be a transparent viscoelastic polymer gel. Such a gel provides a high level of cushioning with durability suitable for extended use and reuse after washing.

The viscoelastic polymer gel may be hydrophobic in character. Such hydrophobic materials adhere to skin without use of adhesives. Further, such materials resist infiltration by sweat and spilled water-based fluids. They may be readily cleaned with soap and water to recover skin adherency after extended use. Once cleaned, cushions formed of such materials may be stored by applying a release liner to the lower surface that keep the surface free of contaminants and retains adherency until needed.

In use, a cushion may be removed from a release liner (not shown) and applied to a portion of the foot. It may be later removed from the foot, washed, and returned to the release liner. The cushion may subsequently be applied to the same or a different portion of the foot.

The viscoelastic polymer gel may be thermosetting in character. Thermosetting materials allow for casting of the cushion in a predetermined shape at low cost. Once cast, such cushions retain their as-cast shape despite changes in temperature in storage and use.

The thickness of the cushion is dependent on the amount of cushioning to be provided which depends both on the sensitivity of the foot and on the compliance of the cushioning material. I have discovered that use of commercially available viscoelastic polymer gels that are transparent provide adequate cushioning in some embodiments when the thickness of the cushion is less than about 0.200". In some embodiments, the thickness may be in the range of about 0.020" to about 0.200". The thickness in some embodiments may be in the range of about 0.040" to about 0.150" and in some embodiments is about 0.090" thick. Thickness above about 0.020" may provide adequate cushioning for many applications. Thicknesses below about 0.200" may retain adequate flexibility and avoid interference with footwear. Thicknesses in the range of 0.040" to 0.0150" provide a good compromise between flexibility and cushioning while avoiding interference with most footwear. A thickness of about 0.090" combines excellent flexibility and cushioning.

Application

The limitations in the angle, extent, and termination of the notch advantageously allows the cushion to assume a variety of shapes while in contact with different portions of the foot. For example, on a smoothly curved portion of the foot, such as the plantar aspect of the arch or the dorsum overlaying the metatarsals, the cushion may attach without buckling by reducing the width of the notch. That is, first notch edge 20 may be disposed more closely to second notch edge 22 than would be case were the cushion applied to a flat surface. This proximation of edges 20 and 22 allows cushion 1 to assume a degree of curvature. As notch edge 20 more closely approaches notch edge 22, this degree of curvature becomes more pronounced. Thus the initial separation of notch edge 20 and notch edge 22 makes available a range of curvatures without overlapping of the notch edges or buckling of the cushion body. Without the notch, or with a notch which is too narrow for the anatomical curvature, either overlapping or buckling would produce a thickened section of the cushion. Such thickened sections are detrimental to the cushioning function because they concentrate pressure in the thickened region and heighten discomfort.

Some portions of the foot are more complexly curved. For example, the lateral malleolus (the bony protuberance about which the foot pivots) blends in a convex curve into the dorsum of the foot but connects in a concave curve with the lateral aspect of the foot inferior to the lateral malleolus. By aligning notch 3 with the inferior boundary of the lateral malleolus, the notch allows one portion of the cushion to freely flex into a convex surface attached to the malleolus and the dorsum. The opposite side of the notch may be displaced medially so that it attaches below to the lateral malleolus. The section of the cushion below the notch may flex separately from the convex surface because the notch decouples flexure of the two sections. Thus the notch allows a section of the cushion to attach to a first portion of the foot without straining the attachment to a second section of the cushion to another portion. The cushion may thus attach to portions of the foot with complex geometry.

On portions of the foot with still more complex geometry, the cushion with the suitably dimensioned notch feature provides a unique cushioning capability. A common spot for irritation in footwear is where the inner surface of the back of a shoe chafes against the back of the wearer's heel. The cushion of the invention may be applied over the back of the wearer's heel (FIG. 4) covering the posterior aspect of the calcaneus. By orienting the notch vertically so as to align with the tendon of the calcaneus (the Achilles tendon), the cushion may assume a shape that conforms smoothly to the surface of the heel and to either side of the tendon without covering the posterior aspect of the tendon itself. This provides cushioning for the back of the foot without interfering with the motion of the tendon. This configuration is particularly advantageous because the tendon of the calcaneus contracts and elongates with each step, and this motion is most pronounced on the posterior aspect of the tendon. By gripping the surface of the skin where movement is less pronounced while leaving the site of greatest motion free, the cushion may remain safely in position without risk of dislodgement by tendon motion. Further, this configuration avoids placing undue constraint on tendon motion, which may in itself lead to foot discomfort.

Figure 5:
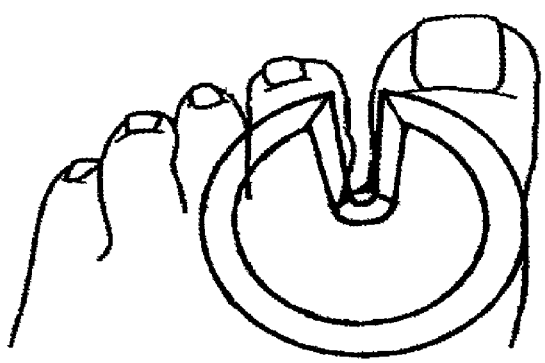
FIG. 5 illustrates an embodiment applied to a location on the dorsum of a human foot.
Figure 6:
FIG. 6 illustrates an embodiment applied to the plantar surface of a human foot.

On still other portions of the foot, the structure of the cushion permits placement to protect and cushion where footwear provide local pressure extremes. For example, many types of sandals include a post or connection that passes between the great toe and the second toe which then branches into straps extending laterally and posteriorly. Such straps or posts may irritate the web space between and behind the toes which, absent such footwear, is not normally a wear surface. The cushion of the invention may be applied over the dorsum of the foot such that the notch aligns with the space between the great toe and the second toe (FIG. 5) to permit passage of the post. In this orientation, the substance of the cushion on one side of the notch would extend over the great toe and could wrap partially around it on the medial side. The substance of the cushion on the other side of the notch might extend laterally over a portion of the other toes while that portion of the substance of the cushion opposite the notch would align with a more posterior portion of the dorsum of the foot. The cushion would thus prevent direct contact between the straps and the foot and thereby prevent or ameliorate any irritation the straps might produce.

The cushion of the invention may thus be advantageously placed in a wide variety of places on the foot. The cushion may of course also be placed in other areas of the body where cushioning is beneficial.

While the foregoing is directed to certain preferred embodiments of the present invention, other and further embodiments of the invention may be devised without departing from the basic scope of the invention. Such alternative embodiments are intended to be included within the scope of the present invention. Moreover, the features of one or more embodiments of the invention may be combined with one or more features of other embodiments of the invention without departing from the scope of the invention. The present invention is intended to be described solely by reference to the appended claims, and not limited to the embodiments disclosed.

I claim:

1. A flexible device to cushion a foot of a wearer, the device comprising:
    a substantially circular planar body;
    a notch formed in the body, the notch including an extended base, a first edge, and a second edge, the base disposed near the center of the body, the first edge running from a first point on the circumference of the body to a first end of the base, the second edge running from a second point on the circumference of the body to a second end of the base, the first edge inclined at an angle with respect to the second edge,
    wherein the notch extends radially from the circumference of the body a distance less than the radius of the body and wherein the device is capable of adhering to a variety of locations on the foot.

2. The device of claim 1 wherein the body comprises a transparent viscoelastic polymer.

3. The device of claim 2 wherein the polymer comprises a hydrophobic thermosetting gel.

4. The device of claim 1 wherein the base forms a radius connecting the first edge to the second edge.

5. The device of claim 1 wherein the angle is less than about 20 degrees.

6. The device of claim 5 wherein the angle is in the range of about five degrees to about 20 degrees.

7. The device of claim 6 wherein the angle is about ten degrees.

8. The device of claim 1 wherein the notch extends radially from the circumference of the body a distance in the range of about one half of the radius of the body to about one radius of the body.

9. The device of claim 8 wherein the distance is in the range of about two-thirds of the radius of the body to about three-quarters of the radius of the body.

10. The device of claim 1 wherein the body has diameter of about 2.6 inches.

11. The device of claim 1 wherein the body has thickness of less than about 0.200 inches.

12. The device of claim 11 wherein the body has thickness in the range of about 0.040 inches to about 0.0150 inches.

13. The device of claim 12 wherein the body has thickness of about 0.100 inches.

14. The device of claim 1 wherein the body includes an upper surface and a lower surface and the upper surface includes a chamfer.

15. The device of claim 14 wherein the chamfer has slope of less than about 80%.

16. The device of claim 14 further comprising a release liner affixed to the lower surface.

17. A flexible cushion comprising:
    a transparent viscoelastic polymer forming a substantially circular planar body including an upper surface and a lower surface;
    a notch formed in the body, the notch extending radially from the circumference of the body a distance less than the radius of the body;
    and terminating in an extended base disposed near the center of the body;
    a chamfered edge on the upper surface of the circumference of the body; and
    a release liner disposed on the lower surface of the body,
    wherein the body is adherent to human skin and wherein the device is capable of adhering to a variety of locations on the body.

18. The cushion of claim 17 wherein the body has thickness of about 0.100 inches and diameter in the range of about 1.0 inch to about 3.5 inches, and the chamfer has slope of about 70%.

19. The cushion of claim 18 wherein the body has diameter of about 2.6 inches.

* * * * *